United States Patent [19]

Frank

[11] Patent Number: 4,924,872
[45] Date of Patent: May 15, 1990

[54] TUBULAR PRESSURE TRANSDUCER

[75] Inventor: Thomas P. Frank, Dublin, Ohio

[73] Assignee: Medex, Inc., Hilliard, Ohio

[21] Appl. No.: 341,822

[22] Filed: Apr. 24, 1989

Related U.S. Application Data

[63] Continuation-in-part of Ser. No. 7086613, Aug. 18, 1987, abandoned.

[51] Int. Cl.$^5$ ............................................. A61B 5/02
[52] U.S. Cl. .................................. 128/673; 128/675; 128/748
[58] Field of Search ............... 128/672.5, 748, 693, 128/734; 73/753–754, 730; 338/307–308, 314

[56] References Cited

U.S. PATENT DOCUMENTS

| | | | |
|---|---|---|---|
| 2,420,148 | 7/1953 | Ostergren . | |
| 2,976,865 | 3/1961 | Shipley | 128/675 |
| 3,149,492 | 9/1964 | Weinberg | 128/672 X |
| 3,336,807 | 8/1967 | Van Lint et al. | 73/754 |
| 3,545,275 | 12/1970 | Harrison et al. | 128/675 X |
| 3,747,410 | 7/1973 | Nissen et al. | 73/753 |
| 3,748,623 | 7/1973 | Millar . | |
| 3,787,764 | 1/1974 | Andeen et al. | 73/754 X |
| 3,957,037 | 5/1976 | Fletcher et al. | 128/693 X |
| 4,027,659 | 6/1977 | Slingluff | 604/280 X |
| 4,028,276 | 6/1977 | Harden et al. . | |
| 4,065,969 | 1/1978 | Dinwiddie | 73/727 |
| 4,160,448 | 7/1979 | Jackson | 128/673 |
| 4,215,698 | 8/1980 | Nuwayser | 128/734 |
| 4,380,237 | 4/1983 | Newbower | 128/734 X |
| 4,420,980 | 12/1983 | Dunemann et al. | 73/730 |
| 4,425,526 | 1/1984 | Mount | 73/730 X |
| 4,484,479 | 11/1984 | Eckhardt | 73/730 X |
| 4,506,250 | 3/1985 | Kirby . | |
| 4,541,284 | 9/1985 | Guagliumi et al. | 73/754 X |
| 4,576,181 | 3/1986 | Wallace . | |
| 4,600,855 | 7/1986 | Strachan . | |
| 4,610,256 | 9/1986 | Wallace . | |
| 4,706,501 | 11/1987 | Atkinson et al. | 73/730 |

FOREIGN PATENT DOCUMENTS 0041807 12/1981 European Pat. Off. .

OTHER PUBLICATIONS

"Conductive Polymers as Fatigue-Damage Indicators," by J. W. Dally and G. A. Panizza, Experimental Mechanics, 3/72, pp. 124–129.

"Conductive Rubber Pressure Transducers for Fluids Research," by I. Kavrak, The Review of Scientific Instruments, vol. 41, No. 5, pp. 628–631, May 1978.

"New Sensing . . . Conductive Polymer," Jan. 1984, Sensor Review, pp. 23, 24.

"A Load Cell System in Foot Pressure Analysis", by W. V. James, J. V. Orr, T. Juddleston, Engineering in Medicine, MEP Ltd. 1982, vol. ii, No. 3.

Primary Examiner—Angela D. Sykes
Attorney, Agent, or Firm—Wood, Herron & Evans

[57] ABSTRACT

In a blood pressure monitoring system, a transducer which is a conductive rubber tube having conductive terminals at each end,
  and circumferentially spaced conductors connected to said semi-conductive band,
  whereby fluid under varying pressure will cause said insulative tube to expand and contract, thereby causing said semi-conductive band to expand and contract, thereby varying the resistance of the semi-conductive band.

3 Claims, 2 Drawing Sheets

4,924,872

TUBULAR PRESSURE TRANSDUCER

BACKGROUND OF THE INVENTION

This is a continuation-in-part of copending U.S. patent application Ser. No. 07/086,613, filed Aug. 18, 1987, now abandoned.

This invention relates to a fluid (gas or liquid) pressure transducer, and particularly to a blood pressure transducer.

Blood pressure transducers are known. See, for example, U.S. Pat. No. 4,576,181 disclosing a disposable blood pressure transducer and U.S. Pat. No. 4,610,256 disclosing a blood pressure transducer having a disposable dome. Such transducers are complicated, expensive, and somewhat difficult to set up to provide assurance of a complete debubbling, that is, complete removal of air bubbles in the system. Transducers of the type described in the patents referred to above employ a silicon chip forming a pressure sensor, an elastomeric diaphragm on which the chip is mounted, a temperature compensation circuit, a light shield because of the sensitivity of the silicon chip, and a housing mounting all of the foregoing elements in such a way that they can be connected in line with the tubing to which the patient's catheter is connected. The system, including the transducer and tubing, is filled with a saline solution that drips slowly through the catheter, the catheter being inserted into the patient's blood vessel. Thus, the pressure in the blood vessel is transmitted directly via the saline solution through the tubing to the transducer. The sensor is electrically connected to a blood pressure monitor presenting a visual display of the patient's blood pressure.

Less complex in structure is a tubular sensor of U.S. Pat. No. 4,600,855. That system, however, requires a special tube and piezoelectric film surrounding the tube. A complex electric circuit is employed to energize the piezoelectric film to cause the tube to resonate and to monitor the frequencies of resonance.

SUMMARY OF THE INVENTION

An objective of the present invention has been to provide a disposable pressure transducer which is exceedingly simple in its construction, is very inexpensive, and presents virtually no debubbling set up problems.

The objective is attained by providing an elastomeric tube doped with conductive particles so that its resistance changes with changes in pressure. The tube section has conductive terminals intimately connected with it at each end. The tube is inserted, as a transducer, in the fluid pressure system to be monitored. The conductive terminals are connected to the monitoring system, preferably through a bridge circuit, the tube forming one part of a Wheatstone bridge.

It has been found that such a tubular transducer, for example, carbon-doped silicon rubber, provides an excellent monitor of the pressure variations within the fluid system.

When used as a blood pressure transducer, as contrasted to an industrial application, the internal surface of the tube must be coated with a dielectric in order to insulate the electrical portion of the total system from the patient. In addition to being a satisfactory dielectric, the coating must also be biocompatible with the fluid system to which the patient is connected.

An alternative form of the invention involves the formation of an insulative tubing that does not require a dielectric internal coating. In this form of the invention, the tubing itself is a dielectric. A stripe or band of sensor material is deposited on the surface of the tubing to form the sensor. The sensing material could be a conductive polymer, and it could be applied by printing, vapor deposition, etc.

Still another alternative consists of providing a dielectric tube and creating a layer immediately below the surface that is semi-conductive and is formed by ion implantation in accordance with a well known process such as is disclosed in "High Tech Materials Alert," July 1987, page 3. In this embodiment, as well as the former embodiment, the dielectric nature of the tubing isolates the sensing element, be it printed or ion-implanted, from the fluid within the tube whose pressure is to be measured.

Obviously, the straight tubular section in series with the tube connected to the patient's catheter introduces no problem of debubbling. Thus, bubbles which could damp the electrical signals are eliminated as well as any hazardous bubbles that might enter the patient's circulatory system and cause embolism.

BRIEF DESCRIPTION OF THE DRAWINGS

The several features of the invention will become more readily apparent from the following detailed description taken in conjunction with the accompanying drawings in which.

DESCRIPTION OF THE PREFERRED EMBODIMENT

Figure 1:
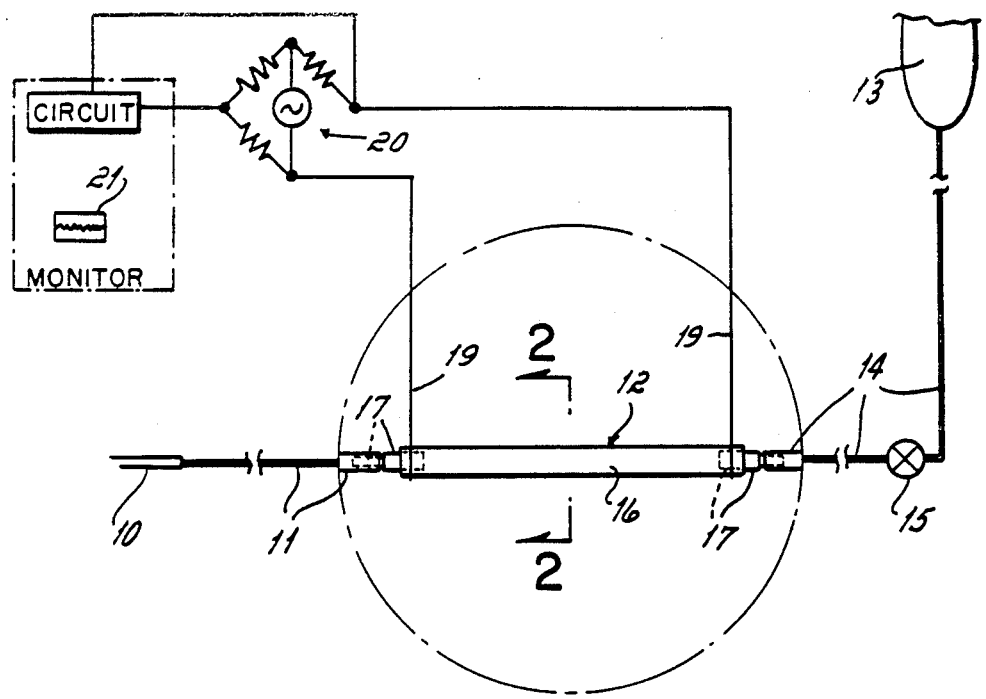
FIG. 1 is a diagrammatic view of the pressure monitoring system, the encircled portion being greatly enlarged for illustrative purposes.
Figure 2:
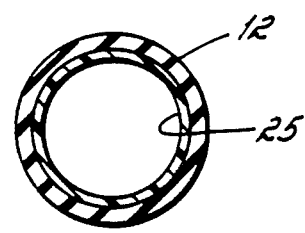
FIG. 2 is a cross section taken along lines 2—2 of FIG. 1.

Referring to FIG. 1, a conventional blood pressure monitoring system is shown. It includes a catheter 10 for insertion into a patient's blood vessel. Pressure tubing 11 connects the catheter to a transducer 12 of the present invention. A bag of saline solution 13 is connected by a tubing 14 and a flush valve 15 to the transducer.

The transducer is a tubular section or tube 16 of an elastomer that has been doped with conductive particles in such a way that its resistance changes in response to pressure applied to it. The tube has, at each end, spigot-type Luer adapters 17. Each adapter has one portion inserted into the end of the tube 16 with the remaining portion projecting from the end of the tubing and adapted to be inserted into the catheter system tubing to make a liquid-tight connection therewith.

Between the ends of the tubular section 12, two conductive terminals 19 are fastened to the exterior surface of the tube. The contact can simply be a surface contact as by wrapping a wire around the circumference of the tubular section. Those conductors are connected to the Wheatstone bridge 20. The transducer is a variable resistance element which is connected via a bridge 20 to a monitor circuit. The bridge and monitor circuit convert the changes in resistance to a visual display indicated at 21. Except for the specific transducer, all of the other elements of the circuit are conventional.

The tubing is preferably a carbon-doped silicon rubber. It has an internal coating indicated at 25. The coating could be deposited on the interior of the tubing or, alternatively, could be laminated to it by means of a co-extrusion process. It is important that the internal coating provide sufficient dielectric protection to provide leakage current protection and defibrillator withstand. It also must be biocompatible with the fluids passing through it so as to avoid contamination of the patient. It must be able to withstand sterilization processes.

It has been found that a short length of tubing which is about 0.250 inch outside diameter, 0.200 in inside diameter and about 2½ inches between conductors provides a good response from the variations in blood pressure normally found in a patient. The spacing between the conductors can be increased or decreased in order to increase or decrease the resistance between them as required for the particular application. The tubing dimensions, durometer, material resistivity can also be varied.

In operation, the variations in blood pressure that are transmitted to the interior of the tubular section 12 cause a pressure to be applied to the tubular section and this alters its resistance. The variations in resistance cause the output from the Wheatstone bridge to vary, thus providing the visual display of the patient's blood pressure.

With suitable modifications, the device is useful with industrial applications.

Figure 3:
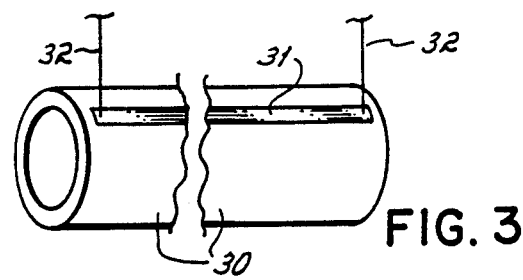
FIG. 3 is a fragmentary perspective view of an alternative form of the transducer.

An alternative from of the invention is illustrated in FIG. 3. There standard tubing indicated at 30 is formed of an insulating polymer. A conductive polymer is deposited in a stripe 31 on the surface of the tubing 30. The conductive polymer could be printed, coated, or vapor deposited onto the surface. When that tubing or a portion of it is placed in a fluid circuit of the type shown in FIG. 1, for example, with conductors 32 connecting the stripe 31 to the Wheatstone bridge 20, variations in pressure within the tubing will be reflected by variations in the resistance between the two conductors 32 of the stripe 31 to provide information at the monitor 21.

Instead of a longitudinally-extending stripe 31, the stripe may be in the form of a circumferential band extending around a substantial portion of the circumference of the tubing 30.

Figure 4:
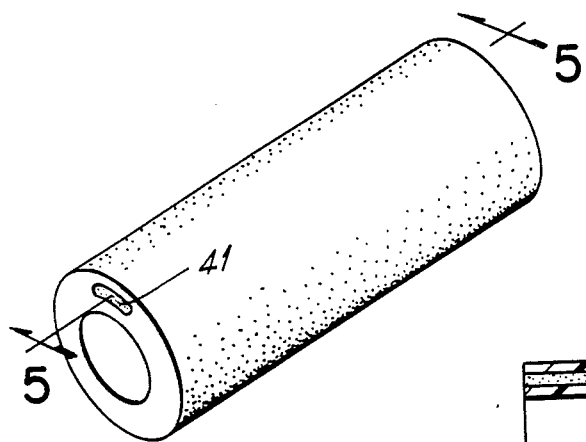
FIG. 4 is a fragmentary perspective view of still another alternative form of the transducer.
Figure 5:
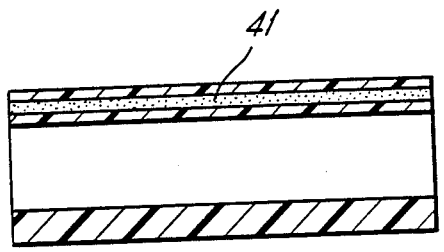
FIG. 5 is a cross-sectional view taken along lines 5—5 of FIG. 4.
Figure 6:
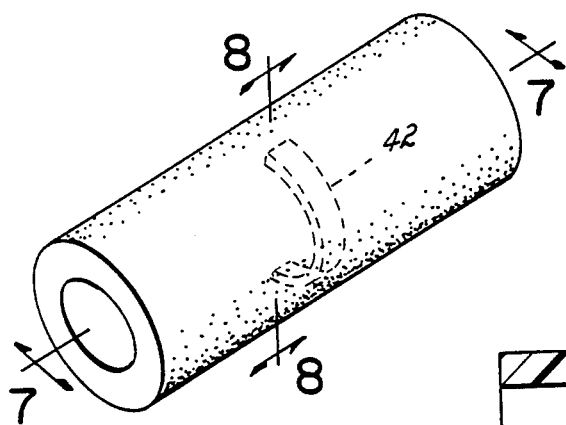
FIG. 6 is a fragmentary perspective view of still another alternative form of the transducer.
Figure 7:
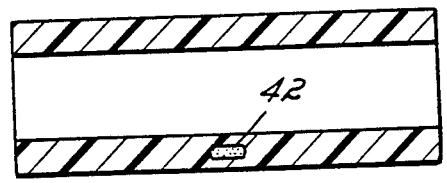
FIG. 7 is a cross-sectional view taken along lines 7—7 of FIG. 6.
Figure 8:
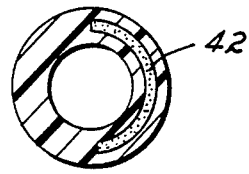
FIG. 8 is a cross-sectional view taken along lines 8—8 of FIG. 6.

Another alternative that consists of forming the sensing element by an ion implantation immediately beneath the surface of the tubing. The ion implantation forms a semi-conductive section whose resistance will vary with changes in pressure in the tubing. It will be in the form of a stripe 41 (FIGS. 4, 5), or a band 42 (FIGS. 6, 7, 8), as in the previous embodiment. Conductors will connect the implant to a bridge as in the previous embodiments.

In the embodiments of FIGS. 3-8, fluid under varying pressure will cause the insulative tubes to expand and contract, thereby causing said stripe or ion-implanted portion to expand and contract, thereby varying the resistance of the stripe or ion-implanted portion. The variation in resistance is proportional to the variation in pressure and the measurement of it, as, for example, by incorporating it in a Wheatstone bridge, will provide a measurement of pressure and variations in pressure.

From the above disclosure of the general principles of the present invention and the preceding detailed description of a preferred embodiment, those skilled in the art will readily comprehend the various modifications to which the present invention is susceptible. Therefore, I desire to be limited only by the scope of the following claims and equivalents thereof:

I claim:

1. A fluid pressure transducer comprising,
   a resilient insulative tube,
   a semi-conductive stripe deposited on said tube,
   and conductors connected to said stripe,
   said combination of resilient tube and stripe creating a sensor that varies in resistance upon expansion and contraction of the stripe when the insulative tube expands and contracts under varying pressure.
2. A fluid pressure transducer comprising,
   a resilient insulative tube,
   ions implanted in the surface of at least a portion of said tube to create a semi-conductive portion of said tube,
   and conductors connected to the semi-conductive portion of said tube,
   said combination of resilient tube and semi-conductive portion creating a sensor that varies in resistance upon expansion and contraction of the semi-conductive portion when the insulative tube expands and contracts under varying pressure.
3. A fluid pressure transducer comprising,
   a resilient insulative tubing,
   a semi-conductive band deposited on and partially surrounding a section of tubing,
   and circumferentially spaced conductors connected to said semi-conductive band,
   said combination of resilient tubing and band creating a sensor that varies in resistance upon expansion and contraction of the band when the insulative tubing expands and contracts under varying pressure.

* * * * *

UNITED STATES PATENT AND TRADEMARK OFFICE
CERTIFICATE OF CORRECTION

PATENT NO.   :   4,924,872
DATED        :   May 15, 1990
INVENTOR(S)  :   Thomas P. Frank It is certified that error appears in the above-identified patent and that said Letters Patent is hereby corrected as shown below:

On the title page:

In the abstract, at the end of line 3, delete "," and insert -- . --

In the abstract, delete lines 4-10 and substitute the following:

-- In alternative embodiments, a nonconductive tube has a semiconductive stripe or band or an ion-implanted stripe or band forming the pressure-responsive element. --

Signed and Sealed this

Third Day of March, 1992

Attest:

HARRY F. MANBECK, JR.

*Attesting Officer*         *Commissioner of Patents and Trademarks*